United States Patent
Broyles (10) Patent No.: US 10,864,124 B2
(45) Date of Patent: *Dec. 15, 2020

(54) TATTOO COVER

(71) Applicant: BEEKLEY CORPORATION, Bristol, CT (US)

(72) Inventor: Mark Broyles, Plainville, CT (US)

(73) Assignee: Beekley Corporation, Bristol, CT (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/694,027

(22) Filed: Sep. 1, 2017

(65) Prior Publication Data

US 2017/0360630 A1   Dec. 21, 2017

Related U.S. Application Data

(60) Continuation of application No. 13/225,804, filed on Sep. 6, 2011, now Pat. No. 9,750,652, which is a division of application No. 12/855,145, filed on Aug. 12, 2010, now Pat. No. 8,012,295, which is a division of application No. 11/121,253, filed on May 3, 2005, now Pat. No. 7,781,041.

(Continued)

(51) Int. Cl.
*A61F 15/00* (2006.01)

(52) U.S. Cl.
CPC ............. *A61F 15/00* (2013.01); *Y10T 428/14* (2015.01)

(58) Field of Classification Search
CPC .. A61F 15/00; Y10T 428/14; Y10T 428/1486; A61N 5/1049; A61B 2090/3937; B32B 9/00; B32B 37/12; B32B 38/00; H05G 1/28; B42D 15/00; B29C 65/48
See application file for complete search history.

(56) References Cited

U.S. PATENT DOCUMENTS

| 168,063 A | 9/1875 | Taylor |
| 2,304,787 A | 12/1942 | Stanton |

(Continued)

FOREIGN PATENT DOCUMENTS

EP   1225208 A1   7/2002

OTHER PUBLICATIONS

3M Health Care, 3M Tegaderm and 3M Tegaderm HP Transparent Dressings, Application Instructions, Copyright 1999, 3M Health Care Prods. and Svcs. Division, London, Ontario, Can.

(Continued)

*Primary Examiner* — Patricia L. Nordmeyer
(74) *Attorney, Agent, or Firm* — McCarter & English, LLP (57) ABSTRACT

An adhesive cover and method of use in which the cover is well-suited to effectively cover a temporary tattoo utilized in radiation therapy treatments. The cover includes a transparent, flexible layer with an optional rigid layer releasably adhered thereto. The first, flexible layer has a lower adhesive surface, an upper low-adhesion surface and a predefined peripheral edge. The second, rigid layer has a lower surface releasably adhered to the upper low-adhesion surface of the first layer, an opposing upper exposed surface, and a peripheral edge cooperative with the predefined peripheral edge of the first layer to preserve the integrity of the first layer during handling and application. The second layer is removed from the first layer only after the first layer is adhered to a patient's skin.

21 Claims, 5 Drawing Sheets

Related U.S. Application Data (60) Provisional application No. 60/629,482, filed on Nov. 19, 2004.

(56) References Cited

U.S. PATENT DOCUMENTS

| | | | |
|---|---|---|---|
| 2,532,011 A | 11/1950 | Dahlquist et al. |
| 2,905,174 A | 9/1959 | Smith |
| RE24,906 E | 12/1960 | Ulrich |
| 3,169,895 A | 2/1965 | Sohn |
| 3,203,125 A | 8/1965 | Stoessel |
| 3,267,623 A | 8/1966 | Block |
| 3,389,827 A | 6/1968 | Abere et al. |
| 3,487,832 A | 1/1970 | Spence |
| 3,655,494 A | 4/1972 | Buzzell |
| 3,895,456 A | 7/1975 | Fabre |
| 4,044,708 A | 8/1977 | Klein |
| 4,112,213 A | 9/1978 | Waldman |
| 4,131,226 A | 12/1978 | Breiter et al. |
| 4,217,164 A | 8/1980 | La Mers |
| 4,310,509 A | 1/1982 | Berglund et al. |
| 4,323,557 A | 4/1982 | Rosso et al. |
| 4,372,303 A | 2/1983 | Grossman et al. |
| 4,454,180 A | 6/1984 | La Mers |
| 4,464,834 A | 8/1984 | Simms |
| 4,499,896 A | 2/1985 | Heinecke |
| 4,506,676 A | 3/1985 | Duska |
| 4,545,371 A | 10/1985 | Grossman et al. |
| 4,558,980 A | 12/1985 | Sturdivan |
| 4,597,206 A | 7/1986 | Benson |
| 4,646,731 A | 3/1987 | Brower |
| 4,664,106 A | 5/1987 | Snedeker |
| 4,737,410 A | 4/1988 | Kantner |
| 4,741,793 A | 5/1988 | Jones |
| 4,787,158 A | 11/1988 | Vitol |
| 4,807,755 A | 2/1989 | Jones |
| 4,822,017 A | 4/1989 | Griesmyer |
| 4,884,563 A | 12/1989 | Sessions |
| 4,987,019 A | 1/1991 | Jones |
| 5,000,172 A | 3/1991 | Ward |
| 5,018,516 A | 5/1991 | Gilman |
| D319,669 S | 9/1991 | Kronberg |
| RE33,727 E | 10/1991 | Sims |
| 5,061,334 A | 10/1991 | Paules |
| 5,088,483 A | 2/1992 | Heinecke |
| 5,106,629 A | 4/1992 | Cartmell et al. |
| 5,127,676 A | 7/1992 | Bockairo |
| 5,153,040 A | 10/1992 | Faasse, Jr. |
| 5,160,315 A | 11/1992 | Heinecke et al. |
| D331,575 S | 12/1992 | Pike |
| 5,188,424 A | 2/1993 | Herron |
| 5,193,106 A | 3/1993 | Desena |
| 5,264,218 A | 11/1993 | Rogozinski |
| 5,266,371 A * | 11/1993 | Sugii .................... A61F 13/023 428/131 |
| 5,306,271 A | 4/1994 | Zinreich et al. |
| 5,310,402 A | 5/1994 | Rollband |
| 5,336,162 A | 9/1994 | Ota et al. |
| 5,372,589 A | 12/1994 | Davis |
| 5,395,675 A | 3/1995 | Altholz et al. |
| 5,407,440 A | 4/1995 | Zinreich et al. |
| 5,411,167 A | 5/1995 | Weder |
| 5,450,046 A | 9/1995 | Kosugi et al. |
| 5,470,351 A | 11/1995 | Ross et al. |
| 5,489,262 A | 2/1996 | Cartmell et al. |
| 5,514,442 A | 5/1996 | Galda et al. |
| 5,520,629 A | 5/1996 | Heinecke et al. |
| 5,531,855 A | 7/1996 | Heinecke et al. |
| 5,573,621 A | 11/1996 | Boreali |
| 5,603,197 A | 2/1997 | Weder |
| 5,657,198 A | 8/1997 | Flener |
| 5,712,767 A | 1/1998 | Koizumi |
| 5,722,943 A | 3/1998 | Sessions |
| 5,738,642 A | 4/1998 | Heinecke et al. |
| 5,743,899 A | 4/1998 | Zinreich |
| 5,752,967 A | 5/1998 | Kritzinger et al. |
| 5,755,681 A | 5/1998 | Plews |
| 5,788,284 A | 8/1998 | Hirst |
| 5,792,092 A | 8/1998 | Turngren |
| 5,800,894 A | 9/1998 | Navis |
| 5,830,550 A | 11/1998 | Treleaven et al. |
| 5,846,623 A | 12/1998 | Denny |
| 5,863,628 A | 1/1999 | Barry |
| D405,116 S | 2/1999 | Anderson, II |
| 5,887,590 A | 3/1999 | Price |
| D408,541 S | 4/1999 | Dunshee et al. |
| 5,891,078 A | 4/1999 | Turngren |
| 5,931,800 A | 8/1999 | Rasmussen et al. |
| 5,951,505 A | 9/1999 | Gilman et al. |
| 6,008,429 A | 12/1999 | Ritger |
| 6,043,406 A | 3/2000 | Sessions et al. |
| D430,674 S | 9/2000 | Dunshee et al. |
| 6,124,522 A | 9/2000 | Schroeder |
| 6,149,614 A | 11/2000 | Dunshee et al. |
| 6,169,224 B1 | 1/2001 | Heinecke et al. |
| 6,237,913 B1 | 5/2001 | Kamille |
| D444,010 S | 6/2001 | Ambrosio |
| 6,269,148 B1 | 7/2001 | Jessop et al. |
| 6,280,549 B1 | 8/2001 | Langan |
| 6,315,480 B1 | 11/2001 | Martel et al. |
| 6,316,073 B1 | 11/2001 | Hiscock et al. |
| 6,350,339 B1 | 2/2002 | Sessions |
| D454,910 S | 3/2002 | Smith et al. |
| D454,955 S | 3/2002 | Dunshee et al. |
| 6,379,790 B1 | 4/2002 | Langan |
| 6,408,916 B1 | 6/2002 | Anderson et al. |
| 6,440,513 B1 | 8/2002 | Kibele et al. |
| 6,543,809 B1 | 4/2003 | Kistner et al. |
| 6,622,728 B2 | 9/2003 | Rusin |
| 6,635,004 B2 | 10/2003 | Conger |
| D483,959 S | 12/2003 | Howard et al. |
| 6,656,558 B1 | 12/2003 | Sarajian |
| 6,685,682 B1 | 2/2004 | Heinecke et al. |
| 6,706,940 B2 | 3/2004 | Worthley |
| 6,708,940 B2 | 3/2004 | Worthley |
| 6,833,128 B2 | 12/2004 | Kamimoto |
| 6,945,936 B1 | 9/2005 | Kerr |
| D517,122 S | 3/2006 | Milliorn |
| 7,342,850 B2 | 3/2008 | Martens et al. |
| 7,559,669 B2 | 7/2009 | Lin |
| D599,849 S | 9/2009 | Halbur et al. |
| 7,625,619 B2 | 12/2009 | Hodson et al. |
| D624,814 S | 10/2010 | Hoppner et al. |
| D642,936 S | 8/2011 | Hoppner et al. |
| D653,286 S | 1/2012 | Haas |
| 8,669,827 B2 | 3/2014 | Popelka et al. |
| 2002/0107466 A1 | 8/2002 | Faasse, Jr. |
| 2002/0115954 A1 | 8/2002 | Worthley |
| 2002/0138024 A1 | 9/2002 | Oladipo |
| 2003/0182815 A1 | 10/2003 | Carlson, II |
| 2004/0116802 A1 | 6/2004 | Jessop et al. |
| 2004/0127838 A1 | 7/2004 | Jeziak |
| 2005/0000133 A1* | 1/2005 | Russell .................. A61B 90/39 40/630 |
| 2006/0139118 A1 | 6/2006 | Vaughn et al. |
| 2010/0047510 A1 | 2/2010 | Couvillion |

OTHER PUBLICATIONS

Deviant Art, "Shapeset 04 Crosshairs," Accessed Aug. 24, 2017, https://www.deviantart.com/art/Shapeset-04-Crosshairs-36547539, dated Jul. 19, 2006, 3 pages.

\* cited by examiner

TATTOO COVER

CROSS-REFERENCE TO RELATED APPLICATION

This application is a continuation application of co-pending U.S. patent application Ser. No. 13/225,804, filed Sep. 6, 2011, entitled "Tattoo Cover," which is a divisional application of co-pending U.S. patent application Ser. No. 12/855,145, filed Aug. 12, 2010, entitled "Tattoo Cover and Related Method," now U.S. Pat. No. 8,012,295 issued Sep. 6, 2011, which is a divisional application of U.S. patent application Ser. No. 11/121,253, filed May 3, 2005, entitled "Tattoo Cover and Related Method," now U.S. Pat. No. 7,781,041 issued Aug. 24, 2010, claiming priority on U.S. Provisional Application Ser. No. 60/629,482, filed Nov. 19, 2004, titled "Tattoo Cover and Related Methods," all of which are hereby incorporated by reference in their entireties.

FIELD OF THE INVENTION

The present invention relates generally to adhesive composites. More particularly, the present invention relates to an adhesive composite providing improved means for handling and application to a surface. The invention is particularly advantageous for use in covering targeting marks or tattoos used in radiation therapy treatments.

BACKGROUND INFORMATION

Adhesive composites including transparent dressings and the like are well known and of countless variety. However, notwithstanding that which is known, there has yet to be provided an adhesive composite that is particularly well suited for covering the temporary marks or tattoos used in radiation therapy treatments.

The first step when an individual requires radiation treatment, after an initial consultation with a radiation oncologist, is a planning session, called a "simulation." The purpose of the simulation is to determine the areas where the radiation will be delivered, called radiation treatment fields, and to plan the treatments. This session is generally conducted by a radiation oncologist, aided by one or more radiation therapists and often a dosimetrist, who performs calculations necessary in the treatment planning. The simulation may last anywhere from fifteen minutes to an hour or more, depending on the complexity of the treatment.

During simulation, a patient lies on a table and a machine or a "simulator" is used to establish the treatment fields. The dimensions and movements of the simulator closely match that of a linear accelerator. The simulator, rather than being used to deliver radiation treatment, is a tool that allows the radiation oncologist and therapist to observe the area to be treated. The simulation may, for example, be guided by fluoroscopy or CAT scan to observe the patient's internal anatomy. The table can be raised and lowered and rotated around a central axis. The lights are usually dimmed while the treatment fields are being set. Temporary marks are made on the patient's skin with magic markers, paint pens, or other suitable means (e.g., carbolfushin). These marks are very important as they enable precise and consistent positioning of the patient so as to ensure that the treatment radiation is properly directed to the appropriate treatment area, and the radiation therapist uses them each session as a guide during the radiation treatment. The treatment plan and treatment fields resulting from the simulation session are verified and radiation treatment is started only after the radiation oncologist and therapists have rechecked the treatment field and calculations, and are thoroughly satisfied with the setup.

Sometimes, after a few treatments, tiny permanent dots called tattoos are used in place of the temporary marks. Other times, permanent tattoos are used initially but due to changing circumstances (e.g., a need to modify the treatment field) temporary marks are subsequently employed. The use of permanent tattoos is particularly advantageous in radiation treatments that extend over weeks as the radiation therapist is able to set up the treatment fields each day with precision, while the patient is allowed to wash and bathe without worrying about obscuring the treatment fields. However, although the permanent tattoos consist of only small pinpricks with a small amount of ink, appearing like a small freckle, there remain instances in which temporary marks are preferable instead of permanent tattoos. Examples of such instances include: (i) when a patient refuses permanent tattoos; (ii) when a facility prefers not to tattoo children; (iii) when the treatment field is highly visible (e.g., the patient's neck or face); (iv) when the skin color makes visibility of the tattoos difficult; and (v) when a facility prefers to use temporary tattoos or marks for an initial number of treatments (e.g., when it is likely that a second treatment field setup is foreseeable). In addition, when it is necessary to employ match lines to match old and new treatment fields, or field borders to distinguish the treatment fields, or radiation boost lines or other similarly notable markings, temporary marks are preferable over permanent tattoos.

A significant advantage associated with the use of temporary tattoos is that the number of such tattoos used need not be limited as do permanent tattoos. Hence, the temporary tattoos provide greater ease, flexibility and freedom in use. Another possible advantage associated with using temporary tattoos as opposed to permanent tattoos is found in that the temporary tattoos can be shaped or sized as needed to facilitate effectively defining the treatment field without the negative consequence of permanently blemishing a patient's skin. The challenge when using temporary tattoos is in keeping them in place on the patient's skin over an extended period of time (e.g., over a typical 6 week radiation treatment). Radiation therapists and facilities, in an effort to address this challenge, currently cover the temporary tattoos using adhesive composites (e.g., Tegaderm™), tape, wound spray, stickers, or the like. For example, radiation therapists often use Tegaderm, which is commercially available in the form of framed sheets of predefined dimension (e.g., approx. 2"×3" sheets). In order to be more effectively used, these framed Tegaderm sheets are manually cut and/or otherwise shaped by the radiation therapist. This cutting/shaping process can be time consuming and inefficient as the Tegaderm, once the frame associated therewith is compromised, becomes difficult to handle and/or otherwise manipulate. The Tegaderm, which is very thin, often wrinkles or folds over itself so that effective application is significantly inhibited. Along these lines, the drawbacks associated with conventional covering techniques are found in the handling of the covering materials, the application of the covering materials and/or the reliability or the lack of durability associated with the covering materials. To date, there has yet to be found a reliable and effective tattoo cover and/or method for keeping temporary tattoos and the like on patients for an extended period of time. Accordingly, the present invention is proposed to address one or more of these and other shortcomings associated with the prior art.

SUMMARY OF THE INVENTION

The present invention is directed to an adhesive composite cover and method of application thereof that addresses one or more of the above-noted shortcomings by providing improved means for the handling and application of a cover to an anatomical surface. The cover is particularly well suited to effectively cover a temporary tattoo utilized in radiation therapy treatments.

In accordance with one aspect, the present invention is directed to an apparatus that is releasably attachable to a portion of a patient's skin having thereon a temporary tattoo or other marking for covering the marking and allowing the underlying marking to be visible therethrough. The apparatus comprises a carrier substrate defining a releasable surface thereon; and at least one cover. The cover comprises a relatively flexible and substantially transparent first layer having an adhesive lower surface releasably superimposed on the releasable surface of the carrier substrate, an upper surface located on an opposite side of the first layer relative to the lower surface, and a configuration enabling it to be 1) removable from the releasable surface of the carrier substrate without substantially wrinkling; and 2) attachable to the patient's skin with the adhesive lower surface adhesively engaging the skin substantially without wrinkling and in a position with the lower and upper surfaces overlying the marking and allowing the underlying marking to be visible therethrough.

In accordance with another aspect, the cover, according to a beneficial feature of the present invention, includes a transparent, first relatively flexible layer with a second, relatively rigid or stiff layer releasably adhered thereto. The second layer is sufficiently firm to maintain its shape under its own weight and the weight of the first layer attached thereto. The first layer has a lower adhesive surface, an upper low-adhesion surface and a predefined peripheral edge. The second layer has a lower surface releasably adhered to the upper low-adhesion surface of the first layer, an opposing upper exposed surface, and a peripheral edge cooperative with the predefined peripheral edge of the first layer so as to be substantially co-terminus therewith.

In an advantageous aspect of an embodiment of the present invention, the second layer is divided into at least two distinct portions by a seam that extends from a first point at the peripheral edge to a second point also at the peripheral edge so that the second layer is separable along or about such seam to facilitate or enable each of the portions to be separately removed from the first layer. In one aspect of such embodiments of the present invention, the first point and the second point are diametrically opposed and divide the second layer into two substantially equal portions. The second layer, in a preferred feature of the present invention, is sufficiently rigid to enable one to hold the cover about the respective peripheral edges thereof without compromising the integrity of the first layer. In another aspect of the present invention, the cross-sectional width of both the first layer and the second layer are at least substantially the same so as to be substantially co-terminus about the respective peripheral edges thereof.

In accordance with another aspect, the present invention involves a method for applying an adhesive composite cover to an anatomical surface. In accordance with a preferred embodiment of the present invention, the method comprises the steps of:

(i) providing an adhesive composite accommodated by a carrier strip, the adhesive composite including at least two substantially co-terminus layers, a first relatively conformable transparent layer with an adhesive lower surface, an opposing non-adhesive or relatively low-adhesive upper surface, and a first peripheral edge, and a second relatively rigid layer releasably adhered to the upper surface of the first layer, the second layer defining a second peripheral edge;

(ii) removing the adhesive composite from the carrier strip;

(iii) handling the adhesive composite by holding it about the second peripheral edge;

(iv) placing the adhesive composite over an anatomical surface at a desired location with the second layer continuously adhered to the first layer;

(v) applying pressure to the adhesive composite via the second layer to ensure proper adhesion; and (vi) removing the second layer from the first layer to leave the first layer securely adhered to the anatomical surface and thereby provide a protective barrier at the desired location.

Another advantageous aspect of the present invention is directed to a method for conducting a radiation treatment simulation. According to a preferred embodiment of the present invention, the method comprises the steps of:

(i) positioning a patient with respect to a simulation machine suitable to establish one or more treatment fields;

(ii) setting at least one treatment field via the simulation machine;

(iii) utilizing one or more marks made on the patient's skin, such as temporary tattoos, to properly position the patient for treatment; and (iv) covering the one or more marks with a transparent, relatively flexible layer that is continuously supported by a relatively rigid layer during handling and application. The method may further comprise separating the relatively rigid layer from the substantially transparent, relatively flexible layer only after such flexible layer is fully adhered to the patient's skin.

According to a beneficial aspect of the present invention, the first, relatively flexible layer has an adhesive skin-contacting surface, an opposing low-adhesion surface, and a first peripheral edge with the relatively flexible layer having a second, relatively rigid layer releasably adhered thereto via the low-adhesion upper surface. The relatively rigid layer defines a second peripheral edge that advantageously cooperates with the first peripheral edge of the relatively flexible layer to preserve the integrity of the first layer during handling and application. That is, the relatively rigid layer, according to a preferred feature of the present invention, is in continuous contact with the relatively flexible layer during handling so as to facilitate applying the cover free from wrinkles, folds and/or other compromising effects.

These and other aspects and advantages of the currently preferred embodiments of the present invention will become more readily apparent in view of the following detailed description and accompanying drawings.

DETAILED DESCRIPTION OF EMBODIMENTS OF THE INVENTION

Figure 1:
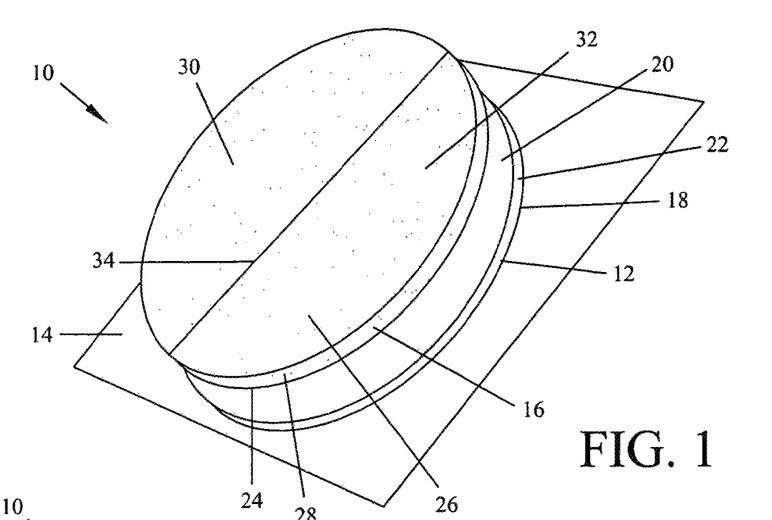
FIG. 1 is an exploded perspective view of a tattoo cover and a carrier strip in accordance with an illustrative embodiment of the present invention.

Referring to the drawings and, in particular, FIG. 1, a tattoo cover in the form of an adhesive composite in accordance with an illustrative embodiment of the present invention is shown and generally represented by reference numeral 10. The cover 10, as shown, is generally circular in shape, which shape is well suited for contouring with a patient's body or anatomical surface thereof. However, other shapes (e.g., oval, rectangular, etc.) equally may be used. The cover 10 includes two layers, a first layer 12 releasably adhereable to a carrier strip 14, and a second layer 16 releasably adhereable to the first layer 12.

The first layer 12 is preferably conformable to anatomical surfaces so as to flexibly move in a complementary fashion with an anatomical surface. Although the first layer 12 may be formed from a variety of different materials and/or composites, particularly well suited materials for use in forming the first layer 12 include elastomeric polyurethane, polyester films or the like. These materials provide the preferred properties of resiliency, high moisture vapor permeability and at least substantial transparency. An example of a suitable commercially available material for use in forming the first layer 12 is 3M 9841 polyurethane available from Minnesota Mining & Manufacturing, which is a thin hypoallergenic, fluid resistant, transparent material conformable to various anatomical surfaces. The first layer 12, as shown, is defined by two substantially planar surfaces; a skin-contacting first lower surface 18 with an adhesive associated therewith and an opposing first upper surface 20, and a first peripheral edge 22 preferably defining a first substantially circular disc shape. The first layer 12, as illustratively shown via broken lines in FIG. 3, may also be a composite of two or more layers in which the lower surface of the first layer 12 is defined by a layer providing certain material characteristics while the upper surface of the first layer 12 is defined by another layer providing the same or different material characteristics.

The adhesive suitable for use with the first lower surface 18 can be any of the conventional adhesives typically used in skin-contacting applications. Examples of such adhesives are disclosed in U.S. Pat. Nos. Re. 24,906, 3,389,827, 4,112,213, 4,310,509, 4,323,557, and 4,737,410, each of which is hereby incorporated by reference. Suitable adhesives for use in the present invention, including for instance those elaborated on in the above-identified references, preferably transmit moisture vapor at a rate greater than or equal to that of human skin. The skin-contacting surface 18 is associated with the carrier strip 14, during non-use (FIGS. 6 and 7), so as to be protected thereby. The carrier strip 14 may be formed from any of a variety of materials. For example, suitable materials include paper based products (e.g., Kraft paper), polypropylene, polyethylene, polyester or any combination of these materials. The carrier strip 14 can be provided with a release coating (e.g., a silicone release material).

The first upper surface 20 of the first layer 12 is suitable for printing so as to allow information to be communicated thereon. For example, product information may be provided so as to allow for ready recognition of the product source (e.g., a trademark). The first upper surface 20 is preferably adhesive free. However, in alternative aspects of the present invention, the first upper surface 20 may be provided with a low-adhesion coating such as, for example, a solution of polyvinyl n-octadecyl carbamate as disclosed in U.S. Pat. No. 2,532,011, which is hereby incorporated by reference. It will be readily understood by those skilled in the pertinent art from the present disclosure that any of a variety of other coatings suitable for providing appropriate low-adhesion properties or a low-adhesion bond equally may be used in accordance with the present invention.

The second layer 16, which is preferably substantially stiffer than, or relatively rigid in comparison to, the first layer 12, cooperates with the first layer 12 so as to maintain the integrity thereof during both handling and application. Suitable materials for use in forming the second layer 16 include, but are not limited to, polyethylene/vinyl acetate copolymer-coated papers and polyester or polyurethane films. An example of a particularly suitable commercially available material for use in forming the second layer 16 is 3M 9842 polyurethane available from Minnesota Mining & Manufacturing. Those skilled in the pertinent art will readily recognize from the present disclosure that any of a variety of other materials and/or combinations thereof equally may be utilized in forming the second layer 16. For instance, as illustratively shown via broken lines in FIG. 3, the second layer 16, like the first layer 12, may be a composite of two or more layers in which a lower surface of the second layer 16 is defined by a layer providing specific material characteristics while an upper surface of the second layer 16 is defined by another layer providing the same or different material characteristics.

Figure 2A:
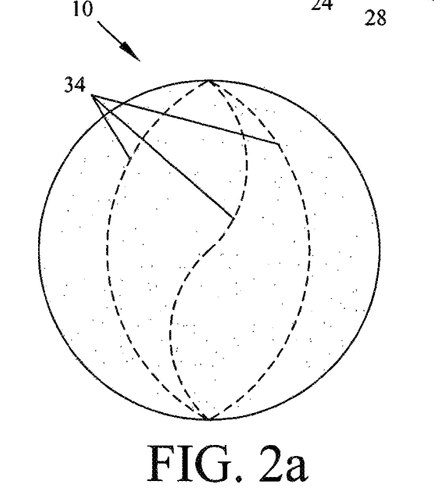
FIG. 2a is a plan view of the tattoo cover of FIG. 1 illustrating with broken lines exemplary curvilinear seams in a layer of the tattoo cover.
Figure 2B:
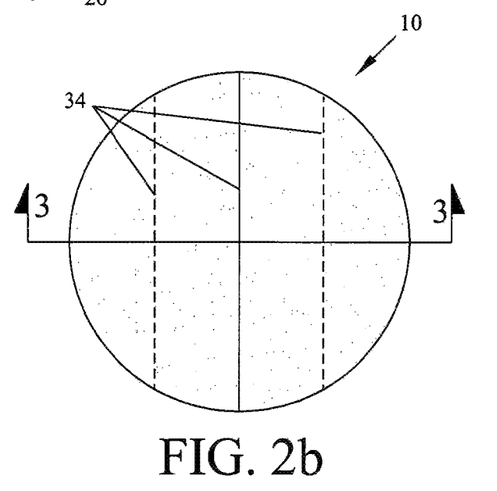
FIG. 2b is a plan view of the tattoo cover of FIG. 1 illustrating with broken lines exemplary seam dispositions in a layer of the tattoo cover.

The second layer 16, as shown, is defined by two substantially planar surfaces; a second lower surface 24 releasably adhered to the first upper surface 20 of the first layer 12 and an opposing exposed second upper surface 26, and a second peripheral edge 28 preferably defining a second substantially circular disc shape. The second peripheral edge 28, as shown, is substantially coincident or co-terminus with the first peripheral edge 22 of the first layer 12. In addition, the second layer 16 is divided into two portions 30, 32 that cooperate to define a seam 34 extending diametrically across the second layer 16 such that the second layer 16 is breakable or easily bent about or along the seam 34 to enable each of the portions 30, 32 to be separately released from the first layer 12. The seam 34, in one aspect of the present invention, traverses the center of the second layer 16 so that the two portions 30, 32 are substantially equally sized and shaped. In other aspects of the present invention, the seam 34 is offset with respect to the center of the second layer 16. Additionally, although the seam 34 is preferably a straight line, it need not be. For example, the seam 34, in another aspect of the present invention, can have curvilinear characteristics associated therewith, such as the exemplary curvilinear shapes illustrated in broken lines in FIG. 2a. A curvilinear or non-linear seam 34 may be used to provide further support to the first layer 12 as such seams are less likely to allow the two portions 30, 32 of the second layer 16 to fold about the seam. Furthermore, in still other aspects of the present invention, the second layer 16 can be provided with any of a number of additional seams, as shown typically in broken lines in FIG. 2b, so as to divide the second layer 16 into any of a number of distinct portions.

The second lower surface 24 of the second layer 16 is, in a preferred aspect of the present invention, provided with a low-adhesion coating such as, for example, the solution of polyvinyl n-octadecyl carbamate disclosed in U.S. Pat. No. 2,532,011, previously incorporated by reference, for effectuating an appropriate bond between the first upper surface 20 of the first layer 12 and the second lower surface 24 of the second layer 16. It will be readily apparent to those skilled in the pertinent art from the present disclosure that any of a variety of other coatings suitable for providing appropriate low-adhesion properties equally may be used. In addition, as previously noted, in alternative aspects of the present invention, the first upper surface 20 of the first layer 12 may also be provided with an adhesive of some sort as desired to accomplish different objectives.

The second upper surface 26 of the second layer 16, like the first upper surface 20 of the first layer 12, may be suitable for printing so as to allow information (e.g., user instructions) to be communicated thereon.

Figure 3:
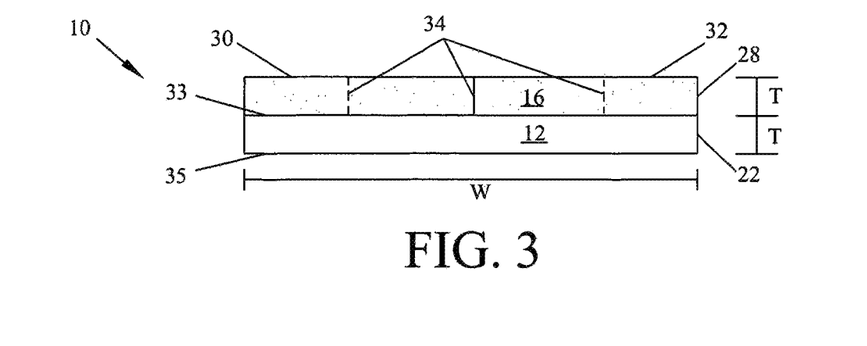
FIG. 3 is a cross-sectional view of the tattoo cover of FIG. 1 taken along line 3-3 of FIG. 2b and removed from the carrier strip.

Referring now to FIG. 3, the second layer 16 provides rigidity to the first layer 12 after the first layer 12 has been removed or separated from the carrier strip 14 (FIG. 1). As shown, the first layer 12 has a thickness "T1" (e.g., about 0.02 mm to about 0.04 mm) and the second layer 16 has a thickness "T2" (e.g., about 0.02 mm to about 0.08 mm). The thicknesses T1 and T2 associated with the respective first and second layers 12 and 16 each may be modified for different applications or purposes as desired. The peripheral edge 28 of the second layer 16, as also shown, preferably corresponds to the peripheral edge 22 of the first layer 12 so as to be substantially co-terminus. Thus, both the first layer 12 and the second layer 16 preferably have substantially the same cross-sectional width or diameter "W" (e.g., preferably within the range of about 10 mm to about 40 mm, and most preferably within the range of about 20 mm to about 30 mm). Accordingly, in a preferred aspect of the present invention, the second layer 16 is sufficiently rigid so as to allow one to handle the entire cover 10 by grasping about the peripheral edge of the second layer 16 without compromising the integrity of the first layer 12. Thus, the cover 10, in a preferred aspect of the present invention, may be effectively handled prior to and during the application thereof without the use of additional structures (e.g., tabs, handles, etc.), which may tend to complicate the process of manufacturing the adhesive composite of the cover.

It is noted that those skilled in the pertinent art will readily recognize alternative ways in which to facilitate the handling and application of the cover 10. Thus, although the foregoing substantially co-terminus dual-layered cover is preferable for providing a small, compact adhesive composite that may be easily manufactured and/or formed, other configurations also may be used and fall within the scope of the present invention. For example, any part of the peripheral edge 22, 28 associated with either or both of the two portions 30, 32 of the second layer 16 can be modified to extend beyond the peripheral edge 22 of the first layer 12 so as to provide means for holding the cover 10 after removal from the carrier strip 14 without contacting the adhesive associated with the first lower surface 18 of the first layer 12. Alternatively, either of the two portions 30, 32 of the second layer 16 can be modified to extend beyond the seam 34 so as to overlap at least a part of the other of the two portions 30, 32 and thereby provide means to grip and/or remove the portion from the first layer 12.

The bond between the second lower surface 24 of the second layer 16 and the first upper surface 20 of the first layer 12 is preferably stronger than the bond between the first lower surface 18 of the first layer 12 and the carrier strip 14. This differential preferably ensures that the second layer 16 remains adhered to the first layer 12 when the cover 10 is removed from the carrier strip 14.

Figure 4A:
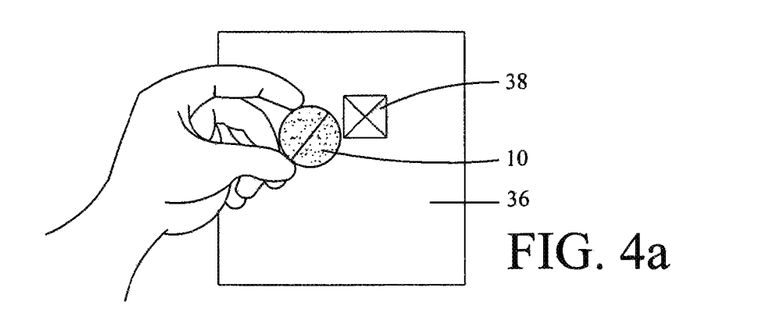
FIGS. 4a, b, c and d are schematic views showing a method of applying the tattoo cover according to an illustrative aspect of the present invention.
Figure 4B:
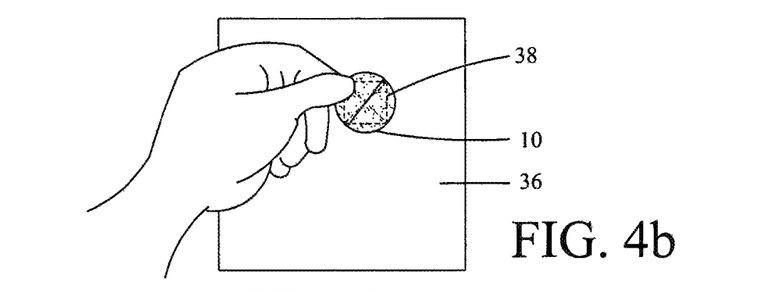
Figure 4C:
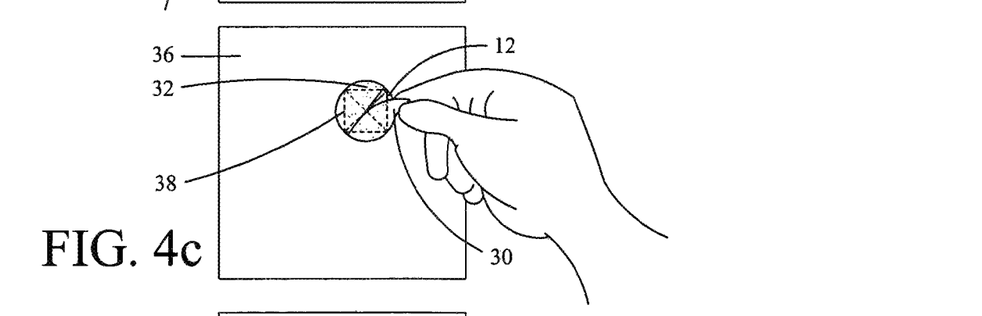
Figure 4D:
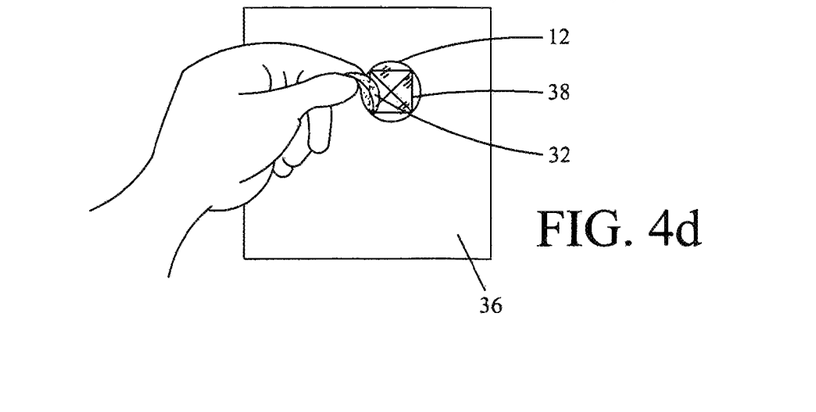

With reference to FIGS. 4a through 4d, applying the cover 10 to an anatomical surface 36 involves first removing the cover 10 from the carrier strip 14 while leaving the first layer 12 and second layer 16 intact. As shown in FIG. 4a, the removed cover 10, after removal from the carrier strip 14, can be held at or about the periphery thereof while being placed over the anatomical surface 36 at a desired location 38. As shown in FIG. 4b, once in place, pressure can be applied to ensure good adhesion between the first layer 12 and the anatomical surface 36. After the cover 10 is appropriately adhered to the anatomical surface 36, each portion 30, 32 of the second layer 16 is removed from the first layer 12 as shown in FIGS. 4c and 4d to leave the first layer 12 securely adhered to the surface 36 and thereby provide a protective barrier at the desired location 38. Thus, the integrity of the first layer 12 in maintained, via the relative rigidity of the second layer 16, during both handling and application. That is, the first layer 12 is prevented from becoming folded, wrinkled or otherwise compromised by the second layer 16 while being removed from the carrier strip 14 and while being placed on and adhered to the surface 36. Consequently, an improved adhesion is achieved between the first layer 12 and the surface 36 as wrinkles, creases, punctures and/or other adhesion imperfections are substantially reduced or eliminated.

Figure 5:
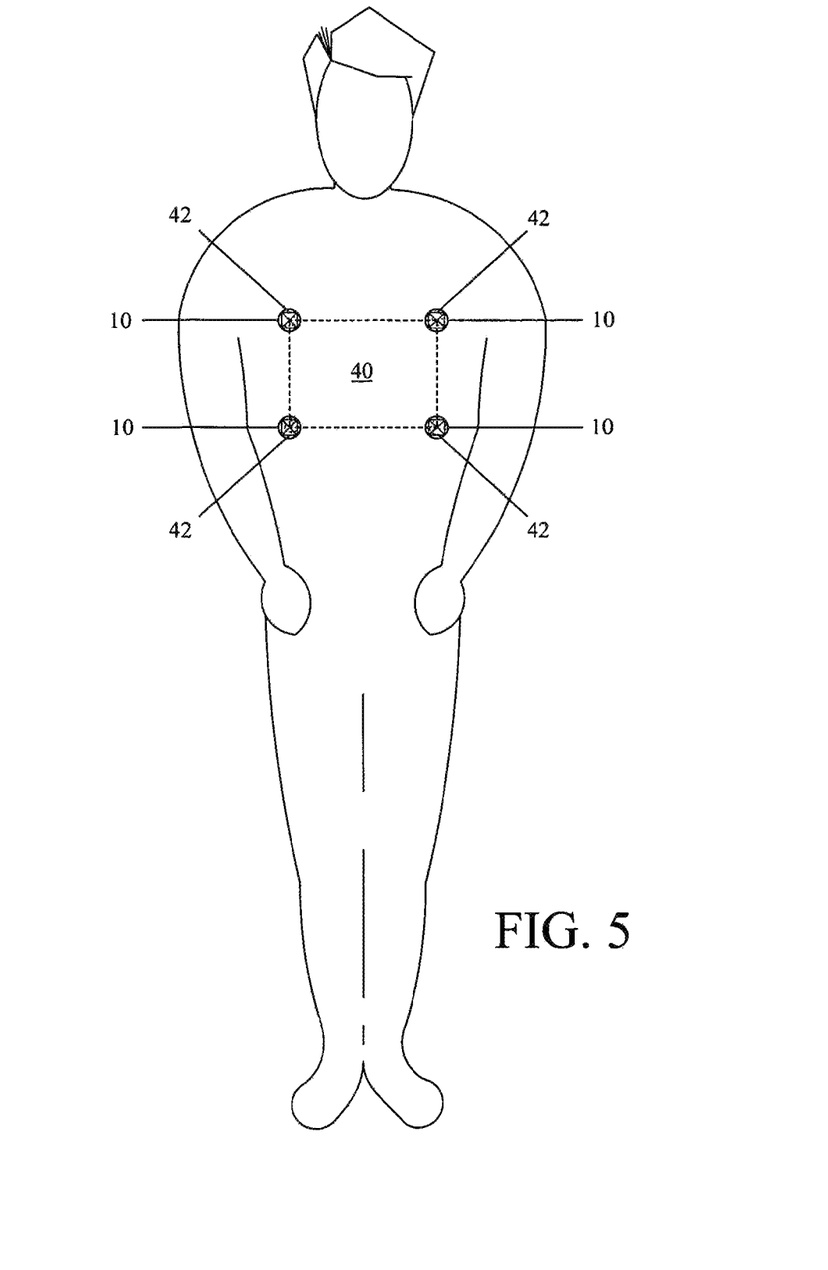
FIG. 5 is a schematic illustration showing a number of tattoo covers placed on a patient so as to aid in properly positioning the patient for a radiation treatment.

Thus, it will be readily understood by those having skill in the pertinent art from the present disclosure that the exemplary cover and corresponding method of applying such as provided herein, is well suited for use in radiation therapy treatments. More particularly, the cover and method of the present invention are well suited for use in keeping temporary tattoos on patients for an extended period of time during radiation therapy treatments. For example, as shown in FIG. 5, during the simulation step of a radiation treatment or at any time subsequent thereto, after one or more treatment fields 40 have been established and the patient properly positioned, via any number of temporary tattoos 42, and the results verified, any one or more of the temporary tattoos can be covered via cover 10 in, for example, the manner previously described with respect to FIGS. 4a through 4d. By so doing, the temporary tattoo may be preserved for a predefined period of time (e.g., about 4 or more weeks) through daily bathing and physical activity.

Accordingly, in practice, a radiation therapist or facility may preserve the temporary tattoos 42 through the entire therapy treatment by utilizing the cover 10 to protect the temporary marks 42 used in positioning the patient so that one or more treatment fields 40 are consistently and properly maintained among different treatment sessions. The covers 10 can be replaced as needed at any time during the therapy treatment (e.g., at week three of a six week treatment) so as to optimize the protective effect provided by such covers. The improved adhesion accomplished between the cover 10 and the anatomical surface 36 when the cover 10 is applied according to the above-described application process results or stems from the first layer 12 being maintained in an extended, relatively rigid state via the second layer 16 during handling and application over the temporary tattoo 42. The transparent or substantially transparent nature of the first layer 12 enables the radiation therapist to readily observe the tattoo 42 and thus allows for the radiation treatment to be conducted according to convention.

Figure 6:
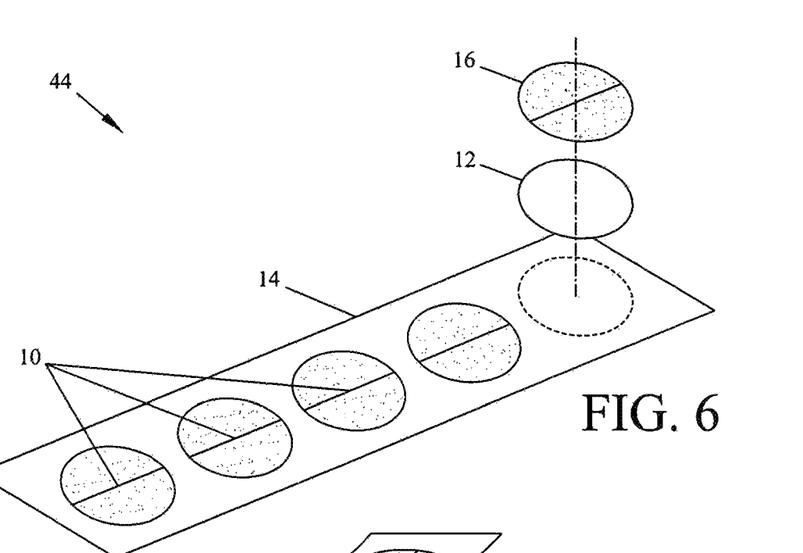
FIG. 6 is a schematic illustration of a number of tattoo covers provided on a sheet carrier strip according to another aspect of the present invention.
Figure 7:
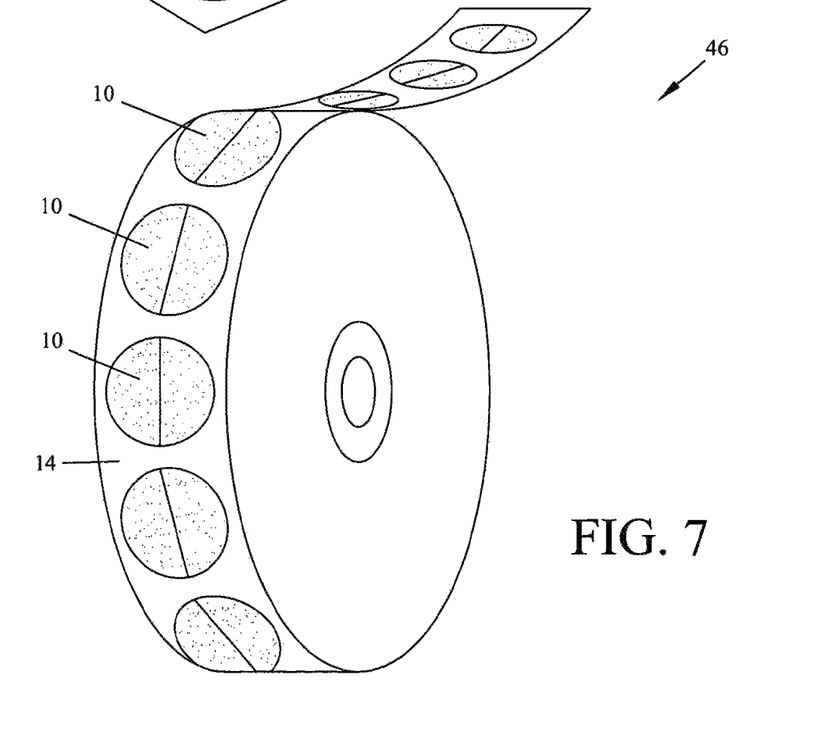
FIG. 7 is a schematic illustration of a number of tattoo covers provided on a rolled carrier strip according to still another aspect of the present invention.
Figure 8:
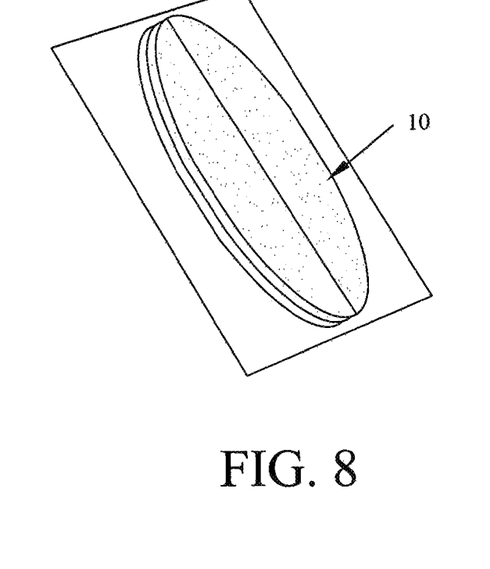
FIG. 8 is a perspective view of a tattoo cover and a carrier strip according to another exemplary embodiment of the present invention.
Figure 9:
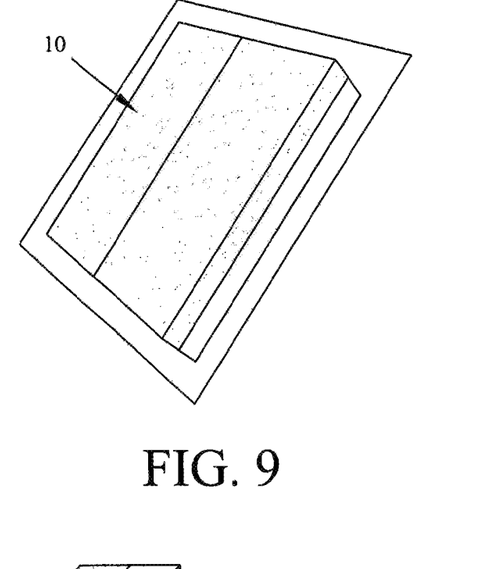
FIG. 9 is a perspective view of a tattoo cover and a carrier strip according to still another exemplary embodiment of the present invention.
Figure 10:
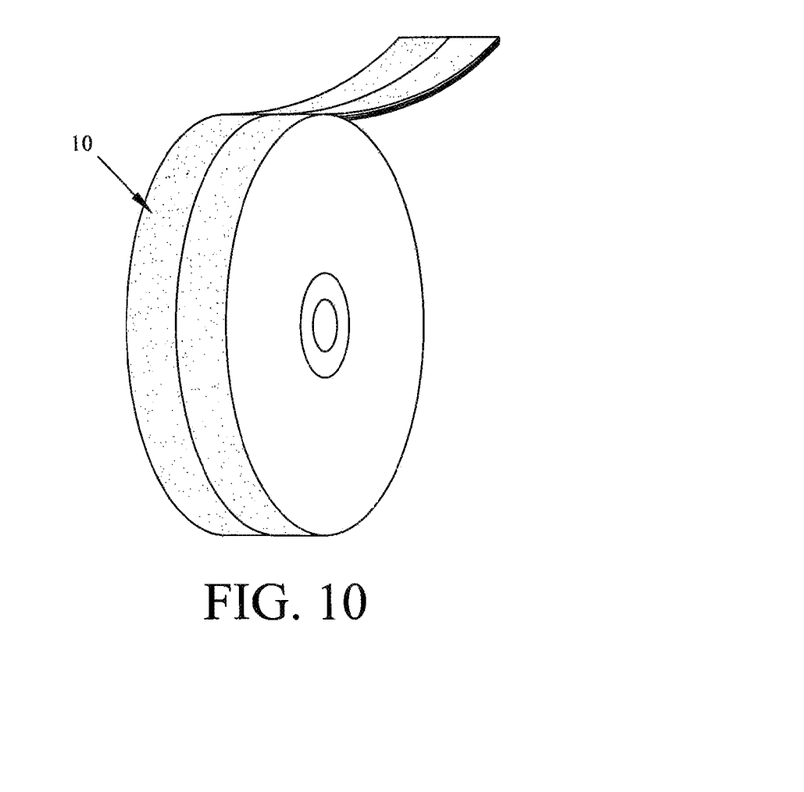
FIG. 10 is a perspective view of a tattoo cover and a carrier strip according to a further exemplary embodiment of the present invention.

As may be recognized by those of ordinary skill in the pertinent art based on the teachings herein, numerous changes and modifications may be made to the above described and other embodiments of the present invention without departing from the scope of the invention as defined in the appended claims. For example, FIGS. 6 and 7 depict different product forms of the cover. FIG. 6 illustrates an exemplary sheet carrier strip 44 suitable to accommodate a predefined number of covers 10. The upper surface of the strip 14 defines a low-friction or releasable surface to allow the covers 10 to be manually gripped and removed therefrom. FIG. 7, on the other hand, illustrates an exemplary product roll or a rolled carrier strip 46 also with a predefined number of covers 10 accommodated thereon. Like the strip 14, the upper surface of the strip 46 carrying the covers 10 defines a low-friction or releasable surface that allows the covers 10 to be manually gripped and removed therefrom. In accordance with another aspect of the present invention, the covers 10 provided on the carrier strip 14 or 46, or other type of carrier strip or substrate, may not include a relatively rigid second layer as described above. For example, if the first substantially transparent layer is sufficiently small and defines a suitable peripheral shape, the transparent layer may be manually engageable and removable from the carrier, and capable of being applied to the desired anatomical surface without wrinkling, without including a second relatively rigid layer overlying the first relatively flexible, transparent layer. In one such embodiment, the covers are substantially circular in shape, and define a diameter within the range of about 10 mm to about 40 mm, and preferably within the range of about 20 mm to about 30 mm. Because of the relatively small diameter of such covers, and the curvilinear shape, the cover can exhibit sufficient rigidity to allow it to be manually gripped and removed from the carrier, and applied to a desired anatomical surface, without wrinkling. Although the currently preferred shape of such covers is circular, other shapes equally may be employed. Preferably, however, such cover defines a substantially continuous curvilinear peripheral shape to facilitate the manual engagement and application of the cover to the desired anatomical surfaces without wrinkling, and to prevent the cover from being accidentally caught or snagged after application to the anatomical surface and removed therefrom either in whole or in part. Additionally, the cover 10, as illustrated in FIGS. 8 and 9, can have any of a variety of different pre-cut shapes and/or sizes including, for example, an oval shape as shown in FIG. 8, or a rectangular shape as shown in FIG. 9. As can be seen, in the embodiments of FIGS. 8 and 9, the covers are provided on single cover carriers or backings, rather than being provided with plural covers on a common backing. Still further, the cover 10 can be continuously linear such as shown in FIG. 10 so as to be cut to length as desired. In another embodiment of the present invention, the linear covers are pre-cut, and are sufficiently small so that they can be provided without a second, relatively rigid layer. In this embodiment, the pre-cut, linear or substantially linear-shaped covers are provided on a common carrier backing or strip, which may be provided in roll form or otherwise, or provided on single-cover carriers or backings. The linear covers without the relatively rigid second layers define a width within the range of about 10 mm to about 20 mm, and a length of about 10 cm or less. As with the relatively small circular or curvilinear covers described above, such linear-shaped covers are sufficiently small that they can be manually gripped and removed from the backing or carrier and applied to the anatomical surface of interest without wrinkling. In other embodiments of the present invention, the covers provided with a second relatively rigid layer include on a peripheral or marginal edge portion of such layer a manually engageable tab extending outwardly from the substantially transparent layer to facilitate manually gripping the cover and applying same to the anatomical surface area of interest. Still further, any of numerous different materials and/or adhesives that are currently known, or that later become known, equally may be used to make the covers and the backings or carriers of the covers of the present invention. Accordingly, this detailed description of the currently preferred embodiments of the present invention is to be taken in an illustrative as opposed to a limiting sense.

What is claimed is:

1. An apparatus that is releasably attachable to a portion of a patient's skin having thereon a temporary tattoo or other marking for covering the marking and allowing the underlying marking to be visible therethrough, the apparatus comprising:
   a continuous carrier substrate defining a releasable surface thereon; and
   a first means on the releasable surface of the continuous carrier substrate, wherein the first means defines a substantially transparent central portion, an adhedsive lower surface, and an opposing upper surface, and is 1) removable from the releasable surface of the carrier substrate without substantially wrinkling, and 2) attachable to the patient's skin with the adhesive lower surface adhesively engaging the skin substantially without wrinkling and in a position with the lower and upper surfaces overlying the marking and allowing the underlying marking to be visible through the central portion.

2. An apparatus as defined in claim 1, wherein the first means is a relatively flexible layer defining the lower surface including an adhesive thereon, the upper surface, and a peripheral edge, wherein the lower surface of the first layer is releasably engageable by the adhesive with the patient's skin in a position overlying the marking and is substantially transparent to allow the underlying marking to be visible therethrough.

3. An apparatus as defined in claim 2, further comprising second means superimposed on the first means and firmer than the first means for manually gripping the respective first and second means while substantially maintaining the shape of the first and second means under their own weight, manually adhesively and removably attaching the respective first means to the patient's skin in a position overlying the marking substantially without wrinkling thereof, and manually gripping the second means and removing the second means from the respective first means adhered to the patient's skin.

4. An apparatus that is releasably attachable to a portion of a patient's skin having thereon a temporary tattoo or other marking for covering the marking and allowing the underlying marking to be visible therethrough, the apparatus comprising:

a continuous carrier substrate defining a releasable surface thereon; and at least one cover comprising a relatively flexible and substantially transparent first layer having a lower surface adhesively and releasably superimposed on the releasable surface of the continuous carrier substrate, an upper surface located on an opposite side of the first layer relative to the lower surface, and a configuration enabling it to be 1) removable from the releasable surface of the carrier substrate without substantially wrinkling; and 2) attachable to the patient's skin with the lower surface engaging the skin substantially without wrinkling, with at least a central portion of the lower surface adhesively engaging the skin, and in a position with the lower and upper surfaces overlying the marking and allowing the underlying marking to be visible therethrough.

5. An apparatus that is releasably attachable to a portion of a patient's skin having thereon a temporary tattoo or other marking for covering the marking and allowing the underlying marking to be visible therethrough, the apparatus comprising:

a carrier substrate defining a releasable surface thereon; and at least one cover comprising a relatively flexible and substantially transparent first layer defining a substantially transparent central portion and having an adhesive lower surface releasably superimposed on the releasable surface of the carrier substrate, an upper surface located on an opposite side of the first layer relative to the lower surface, and a configuration enabling it to be 1) removable from the releasable surface of the carrier substrate without substantially wrinkling; and 2) attachable to the patient's skin with the adhesive lower surface adhesively engaging the skin substantially without wrinkling and in a position with the lower and upper surfaces of the central portion overlying the marking and allowing the underlying marking to be visible therethrough, wherein the outer dimensions of the first layer are less than the outer dimensions of the carrier substrate.

6. An apparatus that is releasably attachable to a portion of a patient's skin having thereon a temporary tattoo or other marking for covering the marking and allowing the underlying marking to be visible therethrough, the apparatus comprising:

a continuous carrier substrate defining a releasable surface thereon; and at least one cover comprising a relatively flexible and substantially transparent first layer defining a substantially transparent central portion and having an adhesive lower surface releasably superimposed on the releasable surface of the continuous carrier substrate, an upper surface located on an opposite side of the first layer relative to the lower surface, and a configuration enabling it to be 1) removable from the releasable surface of the carrier substrate without substantially wrinkling; and 2) attachable to the patient's skin with the adhesive lower surface adhesively engaging the skin substantially without wrinkling and in a position with the lower and upper surfaces of the central portion overlying the marking and allowing the underlying marking to be visible therethrough.

7. An apparatus as defined in 6, wherein the cover includes a manually engageable tab extending outwardly therefrom.

8. An apparatus as defined in 7, wherein the tab is defined by a second layer superimposed on the first layer.

9. An apparatus as defined in 7, wherein the tab is configured to facilitate manual gripping of the cover and applying of the cover to the patient's skin.

10. An apparatus as defined in 6, wherein the cover further comprises a second layer superimposed over the first layer thereof, the first and second layers define first and second peripheral edges respectively, and the first and second peripheral edges are either substantially coterminous or at least part of the second peripheral edge extends laterally outwardly relative to the first peripheral edge.

11. An apparatus as defined in 10, wherein the second layer is firmer than the first layer to at least substantially maintain its shape under its own weight and the weight of the first layer.

12. An apparatus as defined in 10, wherein the second layer is releasably adhered to the upper surface of the first layer.

13. An apparatus as defined in claim 10, wherein the second layer is substantially opaque.

14. An apparatus as defined in claim 10, wherein at least one of the first and second layers is a composite of at least two material layers.

15. An apparatus as defined in claim 10, wherein the first layer defines a thickness within a range of about 2/100 mm to about 4/100 mm, and the second layer defines a thickness within a range of about 2/100 mm to about 8/100 mm.

16. An apparatus as defined in claim 6, wherein the first layer defines one of a substantially circular shape, a substantially oval shape, a substantially rectangular shape, a substantially curvilinear shape, or a substantially rectilinear shape.

17. An apparatus as defined in claim 6, wherein a maximum width or diameter of the first layer is within a range of about 10 mm to about 40 mm.

18. An apparatus as defined in claim 7, wherein the maximum width or diameter of the first layer is within a range of about 20 mm to about 30 mm.

19. An apparatus as defined in claim 6, wherein the cover further comprises a second layer defining at least one seam dividing the second layer into at least two separable portions.

20. An apparatus as defined in claim 6, wherein the lower and upper surfaces extend throughout the first layer.

21. An apparatus as defined in claim 6, comprising a single continuous carrier substrate, and a single cover on the carrier substrate.

* * * * *

UNITED STATES PATENT AND TRADEMARK OFFICE
CERTIFICATE OF CORRECTION

| | | |
|---|---|---|
| PATENT NO. | : 10,864,124 B2 | Page 1 of 1 |
| APPLICATION NO. | : 15/694027 | |
| DATED | : December 15, 2020 | |
| INVENTOR(S) | : Mark Broyles | |

It is certified that error appears in the above-identified patent and that said Letters Patent is hereby corrected as shown below:

In the Claims

Claim 1, Column 10, Line 34, "adhedsive" should be replaced with --adhesive--.

Signed and Sealed this
Second Day of March, 2021

Drew Hirshfeld
*Performing the Functions and Duties of the
Under Secretary of Commerce for Intellectual Property and
Director of the United States Patent and Trademark Office*